United States Patent [19]

Veis et al.

[11] Patent Number: 4,935,497

[45] Date of Patent: Jun. 19, 1990

[54] DENTIN CHONDROGENIC INDUCTIVE AGENT

[75] Inventors: Arthur Veis, Skokie; Bryan S. Sires, Chicago, both of Ill.

[73] Assignee: Northwestern University, Evanston, Ill.

[21] Appl. No.: 241,055

[22] Filed: Sep. 6, 1988

[51] Int. Cl.$^5$ .................... A61K 37/12; A61K 35/12; A01N 63/02; C07K 3/28
[52] U.S. Cl. ..................................... 530/840; 530/300
[58] Field of Search ................................ 530/300, 840

[56] References Cited

U.S. PATENT DOCUMENTS

| | | | |
|---|---|---|---|
| 4,627,982 | 12/1986 | Seyedin et al. | 424/95 |
| 4,774,228 | 9/1988 | Seyedin et al. | 514/21 |
| 4,774,322 | 9/1988 | Seyedin et al. | 530/353 |

*Primary Examiner*—John Kight
*Assistant Examiner*—Carlos Azpuru
*Attorney, Agent, or Firm*—Tilton, Fallon, Lungmus & Chestnut

[57] ABSTRACT

A cartilage-inducing factor has been isolated from dentin and characterized as a polypeptide having an apparent molecular weight of 6,000 to 8,500, an isoelectric pH of from 4.5 to 6.5, and, biologically, as being capable of inducing muscle fibroblast cells to produce cartilage-specific proteoglycan and Type II collagen.

2 Claims, 4 Drawing Sheets

DENTIN CHONDROGENIC INDUCTIVE AGENT

GRANT REFERENCES

Research leading to the present invention was supported in part by grants DE 01374 and DE 08525 from the National Institute of Dental Research.

FIELD OF INVENTION

This invention relates to the bioactive factors in bone and teeth which induce the transformation of fibroblastic cells to chondrocytes, as evidenced by the change in phenotypic cell products, most notably the appearance of a switch from the production of type I collagen (fibroblast) to type II collagen (chondrocyte).

BACKGROUND OF INVENTION

Bone and teeth are known to contain a factor (or factors) which has the capacity to direct commitment of primordial mesenchymal cells towards cartilage and bone formation. Implantation of appropriately decalcified bone or dentin matrix into a soft tissue such as a muscle pouch induces bone formation through a process akin to endochondral ossification. (1) Perivascular mesenchymal cells migrate to the implant and differentiate into cartilage, which then is replaced by true bone. (2)

Koskinen, et al (3) have developed a cell culture assay to detect the presence of chondrogenic activity. This assay is capable of indicating the presence of a chondrogenic factor at the nanogram level. The assay utilizes fibroblast-like cells grown from explants of neonatal rat muscle. These cells can be induced to change to a chondrocyte-like mode of expression. The transformation is followed by assays for cartilage-specific glycosaminoglycan (proteoglycan) and Type II collagen production.

Urist et al. (4) have proposed that the inducing factor in bone is a protein, which they called bone morphogenetic protein (BMP). BMP is reported to be anionic with a relative molecular weight of about 18,500. (4, 8) It can be extracted from an acid demineralized bone matrix with 4.0M guanidine HCl or 6.0M urea+0.5M $CaCl_2$, but the yields are low. Chondrogenic/osteogenic inductive agents have been very difficult to isolate and purify. The absolute amount of these biofactors is very small. Further, they are highly interactive with other bone proteins during isolation, and the assays for their activity have required substantial quantities of the factor.

In 1985, Seyedin et al. reported the characterization of two cartilage-inducing factors derived from bovine demineralized bone. (5) These factors were called CIF-A and CIF-B. Their isolation was by a sequence of extraction, gel filtration, cation-exchange chromatography, and reverse phase HPLC. Both factors were described as having an apparent molecular weight $(M_r)$ of around 26,000. It was further reported that in the presence of 2-mercaptoethanol CIF-A and CIF-B converted to species of about one-half $M_r$, indicating that CIF-A and CIF-B were probably dimers. Subsequently, Seyedin et al. (6, 7) reported that CIF-A and CIF-B were similar if not identical to the transforming growth factor, (TGF-$\beta$) as based on partial sequencing. As pointed out by Seyedin et al. (5), others have reported the extraction of cartilage induction proteins from bone.

Sommerman et al. (9) have reported that human dentin matrix induces cartilage formation in vitro by mesenchymal cells derived from embryonic muscle. Heretofore, however, no one has reported the extraction and purification of the chondrogenic factor in teeth. Other components of dentin matrix have been isolated. Kuboki, et al. (10) reported the preparation of a dentin phosphoprotein, and Butler et al. (11) described the isolation and partial characterization of dentin proteins and proteoglycans. Butler et al. (11) used a preparative method including $CaCl_2$-precipitation of the EDTA extract of dentin, followed by dialysis again of the resultant supernatant, and then passage of the supernatant through a Sephadex G-50 column. A high molecular weight fraction was obtained.

Tsay and Veis (12) have described the preparation of phosphophoryn components of rat incisor dentin, using successive steps of $CaCl_2$ precipitation, ion-exchange chromatography, and gel filtration. The phosphophoryn obtained had a relative molecular weight $(M_r)$ of around 90,000. That procedure utilized the precipitate from a $CaCl_2$ precipitation of the dentin extract rather than working with the supernatant. No chondrogenic factor was prepared.

SUMMARY OF INVENTION

This invention is based on the first isolation and characterization of a cartilage-inducing factor from dentin. This dentin chondrogenic inductive agent (DCIA) differs from the cartilage-inducing agents previously reported to be derived from bone by being of considerably smaller molecular size. The DCIA polypeptide of this invention has an apparent relative molecular weight $(M_r)$ in the range from 6,000 to about 8,500. It probably has an $M_r$ of approximately 8,000. The DCIA polypeptide is apparently a novel compound differing in molecular size from bone-derived chondrogenic inductive agents.

REFERENCE TO DRAWINGS

DETAILED DESCRIPTION

Figure 1:
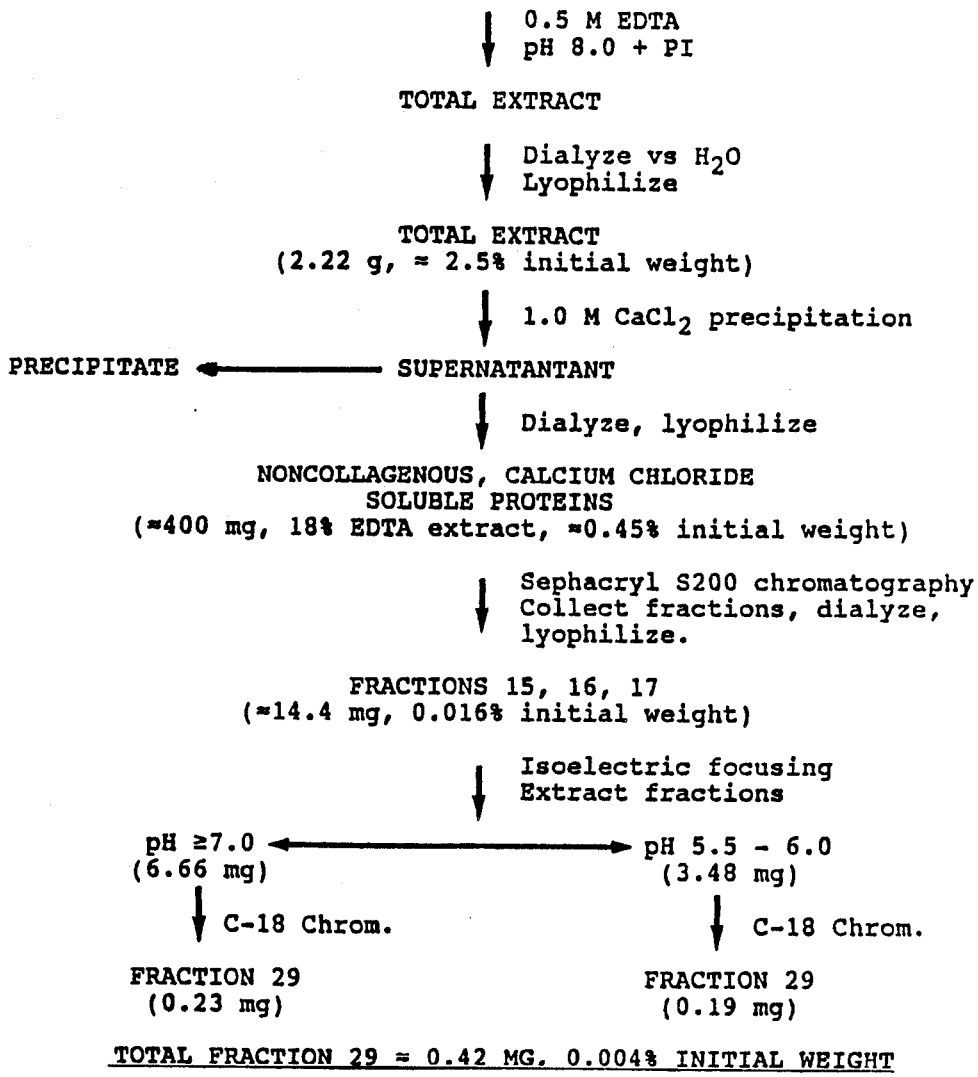
FIG. 1 is a flow diagram illustrating the extraction and fractionation procedure used for preparing DCIA polypeptide.

The DCIA polypeptide can be prepared by the extraction and isolation procedures described in the subsequent examples. In its preferred form, DCIA comprises a pure polypeptide having the following characteristics: (a) extractable from dentin; (b) having an apparent relative $(M_r)$ in the non-aggregated state from 6,000 to about 8,000 as determined by gel filtration chromatography; (c) an isoelectric pH of approximately 6.0; and (d) capable of inducing muscle fibroblast cells in vitro to enhanced production of cartilage-specific proteoglycan and Type II collagen.

Present data indicates that the $M_r$ of the DCIA polypeptide is at the upper end of the 6,000 to 8,500 $M_r$ range. The present approximation is an $M_r$ of 8,000±500. It is believed that the DCIA polypeptide is subject to aggregation, and may also form complexes with other dentin proteins. $M_r$ values set out therefore have reference to DCIA in non-aggregated, non-complexed form.

The isoelectric pH of the DCIA polypeptide is on the acid side, viz. within the pH range from 4.5 to 6.5. Present data indicates that the isoelectric pH is approximately 5.5 to 6.0.

The DCIA polypeptide is further characterized by being capable of inducing fibroblast cells in vitro to produce both cartilage-specific proteoglycan and Type II collagen. A cell culture assay which can be employed for demonstrating these indices of chondrogenic activity is described in Koskinen et al. (3). The proteoglycan determined is precipitable by cetyl pyridinium chloride.

The DCIA polypeptide can be prepared from any mammalian dentin. It has been prepared from rat teeth and bovine teeth. Other preparative procedures can be used. It is anticipated, for example, that the DCIA polypeptide can be made from the DCIA gene using known genetic engineering procedures for gene isolation, cloning and expression.

The experimental basis of the present invention is illustrated by the following examples.

EXAMPLE I

Materials and Methods

A. Dentin Extraction, Fractionation, and Characterization of Fractions

1. Extraction procedures. Maxillary and mandibular incisors were collected from Sprague-Dawley rats approximately 2 months old. Teeth collected fresh or from fresh-frozen rat heads yielded comparable results. All bone, soft enamel, cementum and attached peridontal ligaments were removed mechanically. The teeth were placed in a cold 15% NaCl solution also containing a mixture of protease inhibitors (PI):2.5 mM benzamidine-HCl:50 mM ε-amino n-caproic acid; 0.5 mM N-ehtyl maleimide; and 0.3 mM phenylmethylsulfonyl fluoride. Pulps were removed from the washed teeth with an endodontic file. Further cleaning of the tooth survaces was accomplished by sonicating the teeth in the NaCl-PI solution. Sonication was continued in fresh solutions until the solutions were free of debris. Finally, the teeth were rinsed in cold distilled water and placed in 4M guanidine-HCl at 4° C. and stirred overnight. After a cold water wash to remove the guanidine-HCl the teeth were ready for demineralization. They could be frozen for storage at this stage.

Demineralization and extraction of the soluble dentin proteins was carried out by the procedure of Tsay and Veis (8). The phosphophoryn related components were removed by the calcium chloride precipitation method of Kuboki et al. (9) as modified by Butler et al. (10).

2. Gel filtration. The calcium chloride soluble proteins were fractionated by gel filtration on Sephacryl S-200 in 6.0M guanidine-HCl as described by Price et al. (13). The column effluent was monitored at 226 nm and collected in 4 min fractions at a flow rate of 45 ml/h. Each fraction was dialyzed against distilled water in Spectra/Por tubing, molecular weights cut off 3,500 (Spectrum Medical Industries, Los Angeles).

3. Preparative isoelectric focusing. Preparative isoelectric focusing was carried out in an 8% acrylamide gel using Immobilines (LKB, Sweden) to form a pH gradient (14) spanning the range from pH 4.0 to 7.0. The Immobilines which establish the pH gradient are cross-linked into the gel and remain trapped during elution of the protein bands from the gel. The pH gradient was confirmed by direct measurement with a surface electrode and fractions were cut from the gel in defined pH intervals. The proteins were eluted from the gel slices with phosphate buffered saline (PBS). These solutions were dialyzed into distilled water and then lyophilized. Alternatively, the protein was extracted from the gel slices in the 0.1% trifluoroacetic acid (TFA) solution used for reverse phase HPLC.

4. Acrylamide gel electrophoresis. Polyacrylamide gel electrophoresis was carried out in SDS as described by Laemmli (19) using gels of varying concentrations. For collagen analysis the gels were 6%; for examination of the dentin extract components, gradient gels of 5–15% or 10–20% were used. The gels were stained with silver. Gels for fluorography were first stained in Coomassie Brilliant Blue R-250, then dehydrated and incubated in EN3HANCE (New England Nuclear) for 90 min. The dried gels were exposed to preflashed Kodak XAR-5 film for 72 h at −70° C. The fluorographs were analysed by laser densitometry.

Two dimensional gel electrophoresis was carried out using the ISO-DALT system of Anderson and Anderson (20, 21).

5. HPLC fractionation. Protein fractions were dissolved in 0.1% TFA and passed over a Burdick and Jackson, Inc. OD5 Spherical C-18 Reverse Phase Column (Burdick and Jackson Laboratories, Muskegon, Mich.). Solution A was 0.1% TFA, Solution B was 0.1% TFA-80% acetonitrile. After application of the sample the column was run isocratically until absorbance reached baseline, then a linear gradient was applied. The absorbance was monitored at 226 nm, the column rate was 1 ml/min and 1 min fractions were collected.

HPLC gel filtration was carried out using a Zorbax GF-250 column, run isocratically with a 0.1M $Na_2HPO_4$ buffer solution, pH 7.5. The flow rate was 1.0 ml/min and the absorbance was measured at 230 nm. Fractions were collected at 1 min intervals.

6. Other procedures. Amino acid analyses were carried out using reverse phase HPLC using the precolumn derivitization procedure of Bidlingmeyer et al. (15).

$^{31}P$-NMR analyses were carried out using a Nicolet-200 superconducting magnet resonance spectrometer with 2D-stabilization and operating at 80.988 MHz. The spectrum reported was the average from 72 h of scanning at 23° C. The chemical shift data were reported relative to 85% $H_3PO_4$, in accord with the International Union of Pure and Applied Chemistry recommendations. The spectrum was collected with the sample in 20% $D_2O$, pH 9.0, after removal of divalent cations with Chelex beads.

Sedimentation equilibrium molecular weight determinations were carried out on solutions at a loading concentration of 50 μg/ml of fraction 29 in solvents ranging from 4.0M guanidium hydrochloride to pure water. Runs were made in a Spinco Model E ultracentrifuge equipped with a UV scanner and using an AN-H rotor. The initial speed was 15000 rpm (overspeed) for 1 h, which was then reduced to 12000 rpm. Equilibrium was achieved in about 30 h at 20° C. Absorbance was monitored at 230 nm.

B. Assay for Biological Activity

1. The cell culture system. The cell culture assay was performed essentially as described by Koskinen et al. (3), with only a few but important variations. In brief, explants of neonatal rat muscle were cultured until a lawn of outgrowth cells was established. The minced muscle was removed and the fibroblast-like cells were grown to confluence, passaged twice, then frozen. For assay, $10^4$ thawed cells were seeded in 15 mm wells in 24 well dishes. The cells were grown to confluence in Dulbeccos Modified Eagles Medium (DME) with 10% fetal calf serum (FCS). At confluence the cells were conditioned by culture in DME+2% FCS for 2 days. The conditioning medium was removed and replaced with 0.5 ml of test solution in DME+2% FCS, at concentrations ranging from 10 μg/ml for the crude extracts to 10 ng/ml for the final HPLC purified fractions.

The most important difference from the Koskinen et al. procedure (7) was that after 4 h of incubation the cells were rinsed free of the added protein and fresh DME+2% FCS was added along with either $^{35}$S-sodium sulfate or 3H-proline, to determine the incorporation of $^{35}$S-sulfate and to assess collagen production. Appropriate controls were run for each assay. In other experiments epidermal growth factor (EGF) and/or transforming growth factor β (TGF-β) were also added. The TGF-β preparation had been purified to homogeneity (16) then desalted by reverse phase chromatography on C-18.

2. Incorporation of $^{35}$S-Sulfate into cartilage-specific proteoglycan.

After the 4 h incubation of the conditioned cells with the fraction being assayed, and a wash with DME+2% FCS, 2 μCi/ml Na$^{35}$SO$_4$ were added to each well. Incubation continued for an additional 20 h, then the medium was collected and combined with 2×0.5 ml washes with FCS-free DME. The sulfated glycosaminoglycan content was determined by the method of Saarni and Tammi (17). Each measurement was made in quadruplicate, that is, 4 identical wells were used for each fraction assayed. The cell layers were treated with 0.025% trypsin in PBS and suspended. The cell suspensions were centrifuged and the cells washed with PBS. They were then suspended in 1.0 ml of PBS. After appropriate dilution, cell numbers were determined by direct count using an Ultra Plane grid marked changer (C. A. Hausser and Son). Cell numbers were also determined in quadruplicate. Four or eight wells were used for controls in every assay. Results were reported as counts incorporated per cell per unit weight of test fraction added per ml in the assay well. The specific activity was determined as:

Specific Activity$+([CPM/cell]_{exp}/[CPM/cell]_{cont})-1/(mg/ml)$. For screening purposes a fraction was considered to be active if it produced a 50% increase over control in the CPM/cell incorporated at the concentration used.

3. Production of Type II collagen. The same cell conditioning and incubation protocols as in the sulfate incorporation assays were used except that 2.0 μCi/ml $^3$H-proline was added to each well and the labeling period was extended to 56 h. This longer incubation time was required for the production of sufficient quantities of collagen for the type assay. At the end of the labeling period the media and cell layer proteins were harvested separately. Washes were with sterile PBS. The cell layer was scraped from each well in 1 ml PBS. The media, cells and their washes were placed in microfuge tubes containing ammonium sulfate to make a final concentration of 30% saturation. The protease inhibitor mix described above was included. The collagen precipiatated from solution after standing at 4° C. for 24 h, and was collected by centrifugation at 38,000×g for 20 min at 4° C. The precipitates were solubilized in cold 0.4M NaCl, pH 7.2. Aliquots of these solutions were taken for either gel electrophoresis or enzyme-linked immunosorbent (ELISA) assay using specific Type I and Type II collagen antibodies. In the case of gel electrophoresis, the gels were fluorographed and the ratios of pro-α1(I) to pro-α2(I) chains determined by densitometry. An increase in the ratio was taken as a measure of the appearance of pro-α1(II) collagen chains.

The indirect ELISA procedure of Engvall and Perlmann (18) was used with anti-rat types I, II, III and V.

RESULTS

1. Fractionation and preliminary characterization.

A flow diagram for the extraction and fractionation of the soluble components of rat incisor dentin is shown in FIG. 1. Included in the figure are the total weights recovered in each of the initial fractionation steps. Two hundred seventy one rats yielded 89 g of cleaned moist teeth. The soft enamel had been removed by scraping but the hardened enamel was still present. Following EDTA extraction about 2.5% of the initial weight was recovered as soluble protein. The phosphophoryn component was precipitated with 1.0M CaCl$_2$ following the Kuboki et al. procedure (9, 10). About 0.45% of the initial weight was in the non-precipitable fraction, ≈18% of the EDTA extractable protein.

The incorporation of $^{35}$S-Sulfate into cartilage-specific proteoglycan was the most convenient and rapid assay and was used as the primary method for screening during fractionation. The cell culture assay was used at every step of the procedure and every chromatographic fraction obtined was assayed for its effect in enhancing the incorporation of $^{35}$S-Sulfate into cartilage-specific proteoglycan. Only fractions which clearly enhanced this activity were tested for Type II collagen production.

The CaCl$_2$ precipitate showed no activity beyond background. All of the activity was in the supernate fraction. The unfractionated EDTA extract was inactive, as was a mixture of the precipitate and supernate fractions. This suggested that either a specific calcium ion precipitable inhibitor or the factor was present in the dentin EDTA extract, or that, in the absence of high calcium ion concentrations, the dentin chondrogenic factor interacted with other proteins of the precipitate fraction. On the basis of this result all of the efforts at purification were directed to the fractionation of the activity in the CaCl$_2$ supernatant fraction.

Figure 2:
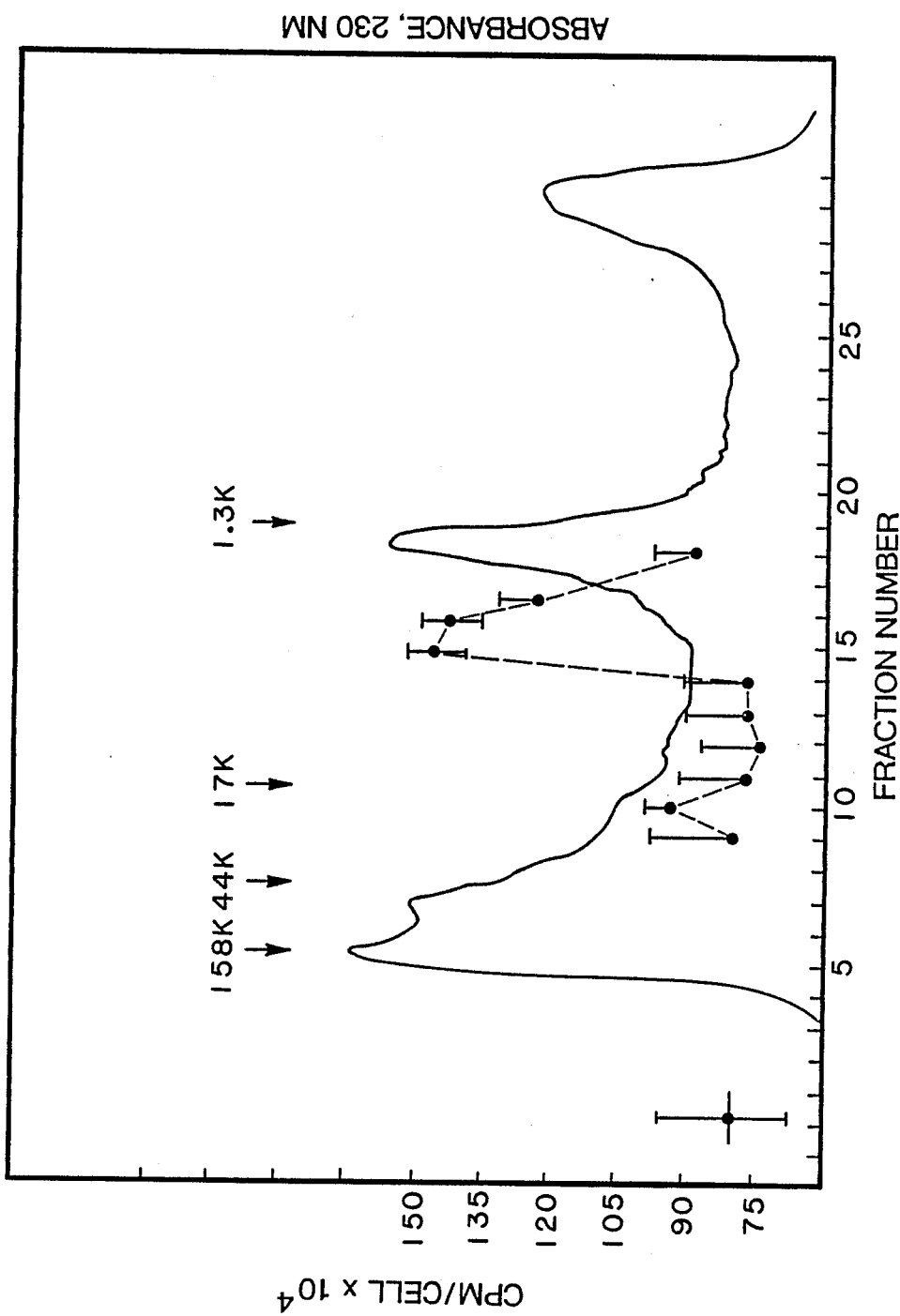
FIG. 2 is a chromatogram of the $CaCl_2$ supernatant fraction on Sephacryl S-200 and 6.0M gunidine.HCl.

The CaCl$_2$ supernatant was chromatographed on Sephacryl S-200 (FIG. 2) in the presence of 4.0M Guanidine-HCl and each fraction was assayed for sulfate incorporation. Fractions 15, 16 and 17 demonstrated activity. The binding fractions were comparable to controls. When examined by 5–15% SDS-PAGE every fraction was found to be quite heterogeneous.

Preparative 1-D isoelectric focusing was carried out on Immobiline polyacrylamide gels in the pH range from 7 to 4. Slices were taken in 0.5 pH unit sections; each section was eluted and the resultant fractions tested for activity. Activity was found in both the pH 5.5–6.0 range and in the fraction at pH≧7. SDS-PAGE showed both fractions to be heterogeneous, but most of the high molecular weight components were in the high pH fraction.

Figure 3:
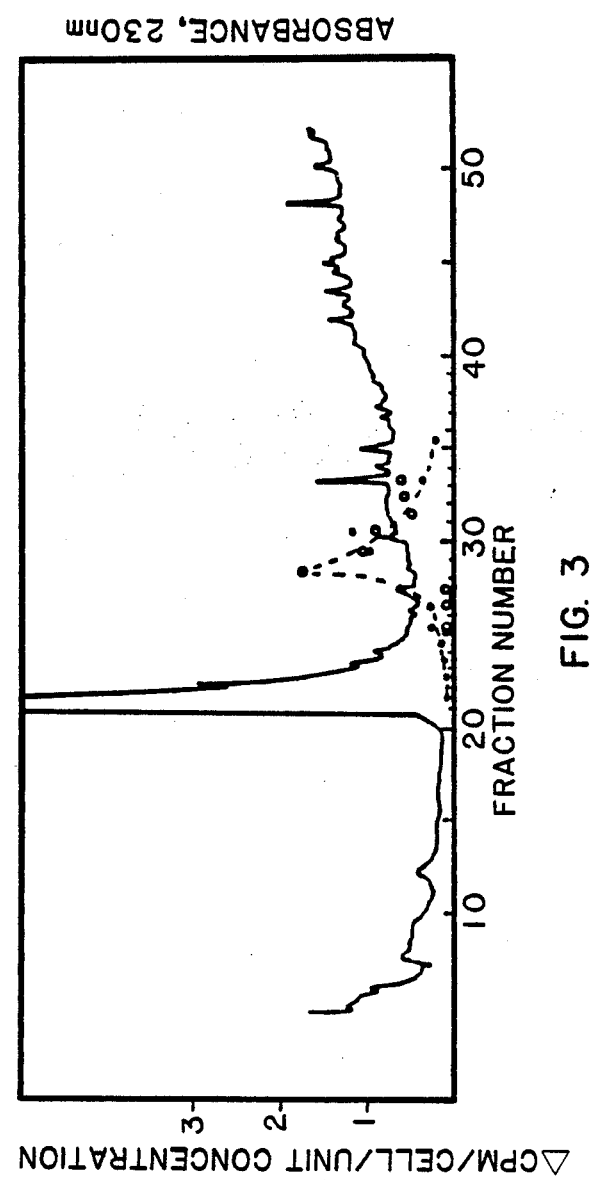
FIG. 3 is a chromatogram of the pH 5.5-6.0 fraction.

The chromatogram of the pH 5.5–6.0 fraction is shown in FIG. 3, along with the activity assay. A small peak at fraction 29 yielded an activity comparable to the cleaner fraction 29 from the pH 5.5–6.0 isoelectric focusing fraction. Fractions 20–25 yielded essentially baseline values. Every fraction from the C-18 reverse phase chromatography was assayed for $^{35}$S-sulfate incorporation.

After biological activity assay of the fractions there was just enough material in the fractions for gel electrophoresis, and single micro amino acid analysis and preliminary amino terminal region sequencing runs.

The protein of fraction 29 was found to be rich in hydrophobic residues, low in content of histidine and arginine, and to contain phosphoserine. The presence of organic phosphate was confirmed by (non-descructive) $^{31}$P-NMR spectroscopy by the appearance of a $^{31}$P peak with an upfield shift of 3.6 ppm from the position of inorganic phosphate and an appropriate broadening.

Figure 4:
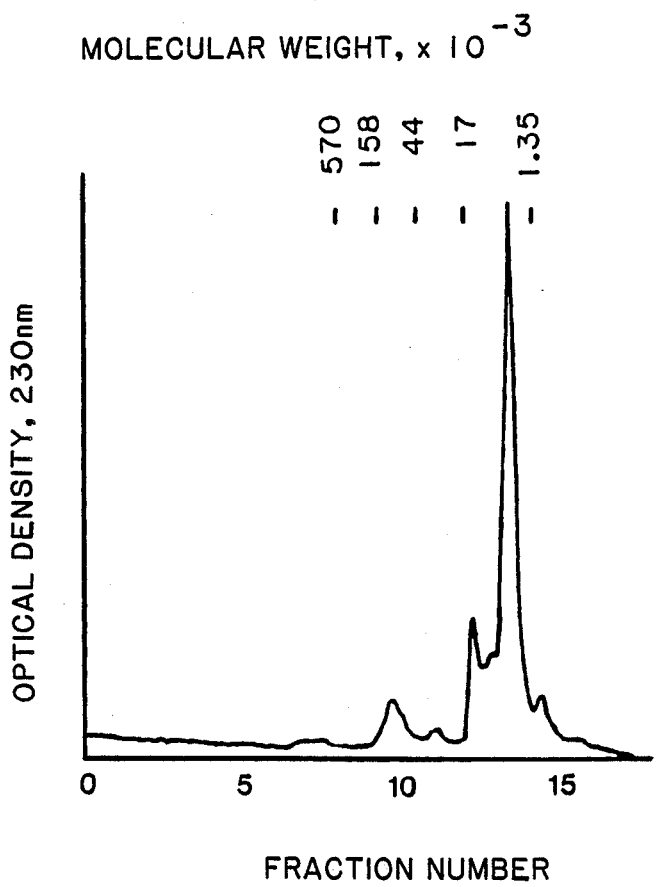
FIG. 4 shows the results of a Zorbax G-250 gel filtration of the Fraction 29 component.

Gel electrophoresis of Fraction 29 in 10–15% gradient gels in the Laemmli system (19) in SDS showed that the principal component had an $M_r$ in the range of 6,000–8,000, but the silver staining characteristics of the fraction were poor and the homogeniety of the fraction remained questionable. In contrast to the behavior of the more crude fractions, fraction 29 was readily soluble in 0.1M $Na_2HPO_4$ at pH 7.5. It was therefore run over a Zorbax G-250 gel filtration column with the results shown in FIG. 4. The column fractions were collected as shown in the chromatograph and analyzed for activity. All of the activity was in fourth peak, the major component. This peak corresponds to an $M_r$ in the range between about 14,000 and 8,000, confirming that the principal gel electrophoresis band represents the active component.

One salient feature of fraction 29 is its tendency to aggregate in non-dissociative solution conditions and even in the presence of SDS during gel electrophoresis. The appearnace of high molecular weight components in the Zorbax gel filtration chromatogram was surprising in view of the prior Sephacryl S-200 fractionation. To examine this further in a non-destructive fashion, fraction 29 was dissolved at physiological ionic strength at neutral pH and an equilibrium ultracentrifugation run was carried out to determine the average molecular weight. It was evident that aggregation took place under the solution conditions and that the weight distribution was quite heterogeneous. The inclusion of 4.0M guanidine hydrochloride led to a reduction in the weight average molecular weight, but the weight average molecular weight was considerably higher than expected from the gel electrophoresis and gel filtration chromatography results obtained under more stringent dissociative conditions (6.0M guanidine.HCl). Self association is evident, however, in the mixtures aggregation may take place preferentially with other proteins.

2. Chondrogenic activity.

Two measures of the activity of fraction 29 were made, an assay for the production of cartilage-specific proteoglycan and electrophoretic and ELISA assays for the production of Type II collagen, respectively, by the methods described in Koskinen, et al. (3). The proteoglycan assay was carried out using the supernatant culture medium. In several analyses the cell layer was also included but accounted for less than 10% of the total sulfate incorporation. The incorporation was clearly a function of the concentration of fraction 29 added to the cells, and at this stage of purification the concentration required to double the incorporation of sulfate into proteoglycan was on the order of 10–50 ng/ml.

The collagen determinations were carried out using the collagen in the cell layer. In order to keep the system as simple as possible no β-aminopropiionitrile was added to the culture medium, the usual procedure for the determination of the total collagen produced in cell culture. When $^3$H-proline was used to label the collagen under the culture conditions the majority of counts were retained in the cell layer. When collagen type II was measured by the ratio of the density of the pro α1/pro α2 bands following gel electrophoresis under reducing conditions, the data clearly showed a concentration dependent increase in the ratio from an initial control value of 2. This could have been the result of an increase in pro α1(I) and a decrease in pro α2(I) (the production of the type I α1 trimer) or the presence of type II collagen. A quantitative immunostaining determination, using a type II antibody, however, showed that type II collagen was present and increased in a dose dependent fashion over the same concentration range of fraction 29 as the electrophoretic ratios of pro α1 and pro α2 bands. There was also an increase in the amount of type I collagen seen but this was only evident when >1 μg/ml concentrations of Fraction 29 were used. There was no change in the baseline absorbance values in ELISA's using antibodies to Type III and Type V collagens.

The assays for Type II collagen and increased cartilage-specific proteoglycan production both showed response to Fraction 29 in the 10–50 ng/ml range and a similar concentration for half-maximal activity. The parallel behavior of the three very different assays suggests that the increased production of proteoglycan and the appearance of Type II collagen may be linked.

EXAMPLE II

A presently preferred modification of the procedure of Example I for preparing DCIA polypeptide in greater yields and higher purity is as follows:

A. Dentin Extraction, Fractionation, and Characterization of Fractions.

1. Extraction procedures. These are carried out exactly as practiced in Example I.A. 1.

2. Gel filtration. The initial fractionation on Sephacryl S-200 is carried out as in Example I.A. 2.

3. HPLC gel filtration. After the fractions of interest have been collected from the dissociative gel filtration in step 2, those fractions with $K_{av}=0.58–0.80$ are combined, dialyzed against distilled water to remove the guanidine, using Spectra/Por tubing with molecular weight cut off of 3500. The dialyzed fraction was lyophilized and then taken up in 0.1M $Na_2HPO_4$, pH 7.5. This solution was passed over a Zorbax GF-250 column and eluted isocratically at a flow rate of 1.0 ml/min. One minute fractions were collected. Cell culture assay showed that maximal activity was distributed in the fractions from 14,000 to 6000 $M_r$. A small quantity of higher and lower molecular weight components were not fractionated further, although the higher weight fractions were obviously aggregates containing some active DCIA.

4. Reverse phase chromatography. The pooled Zorbax fractions were dialyzed to remove the phosphate buffer, then lyophilized. The fraction was then dissolved in 0.1% Trifluoroacetic acid in 5% acetonitrile. This was applied to a Dupont Poly - F C-8 reverse phase HPLC column. The column was eluted with a gradient from 5% to 80% acetonitrile, all at 0.1 % TFA, 2.0 ml/min. Fractions were collected at 0.1 min. intervals.

5. Assays for activity. The assays for DCIA activity were as specified in Example I. Each fraction from step II.A.4 was analyzed for activity. A fraction was identified which was considered to represent a single component peak, and gave an activity in the cell culture assay system with a 3 to 4 times control level incorporation of $^{35}$S- sulfate at a concentration of 1 nanogm/ml.

B. Purity Standard

An operational criteria of purity for the DCIA polypeptide is the appearance of a single symmetrical peak in the reverse phase HPLC as described in Examples I and II. The purified DCIA polypeptide should have a specific activity of at least $5 \times 10^4$ in the cell culture assay system described in Example I, and in Koskinen et al (3). Specific activity is defined as:

$\{[CPM/cell]/[CPM/cell]_{control} - 1\}/$mg DCIA/ml.

REFERENCES

1. Reddi, A. H. (1985) J. Biomed. Mater. Res. 19, 233–239.
2. Reddi, A. H. and Huggins, C. (1972), Proc. Natl. Acad. Sci. 69:1601–1605.
3. Koskinen, K. P., et al. (1985), Connective Tissue Research, 14:141–158.
Urist, M. R., et al. (1971), J. of Dent. Res. 50:1392–1406.
5. Seyedin, S. M., et al. (1985), Proc. Nat. Acad. Sci. U.S.A., 62:2267–2271.
6. Seyedin, S. M., et al. (1986), J. Biolog. Chem., 261:5693–5695.
7. Seyedin, S. M. et al. (1987), J. Biol. Chem. 262(5):1946–1949.
8. Urist et al. (1984), Proc. Natl. Acad. Sci., 81:371–375.
9. Sommermann, M. J. et al. (1987), J. Dent. Res., 66:1551–1558.
10. Kuboki, U., et al. (1979), J. Dent. Res., 58:1926–1932.
11. Butler, W. T., et al. (1981), Coll. Res. 187–199.
Tsay, T. G. and Veis, A. (1985), Biochemistry, 24:6363–6369.
13. Price et al. (1984), International Conference on Chemistry and Biology of Mineralized Tissues, 159–163.
14. Bjellqvist, B. et al. (1982) J. Biochem. Biophy. Methods, 6:317–339.
15. Bidlingmeyer, B. A., et al. (1984), J. Chromatog. 335:93–104.
16. Assoian, R. K. et al. (1983) J. Biol. Chem., 258:7155–7160.
17. Saarni, H. and Tammi, H. (1977) Anal. Biochem., 81:40–52.
18. Engvall, E., et al. (1971) Immunochem., 8:871–874.
19. Laemmli, U. (o970) Nature, 227:680–688.
20. Anderson, N. G., et al. (1978a) Anal. Biochem. 85:331–340.
Anderson, N. L. et al. (1978b) Anal. Biochem. 85:341–354.

We claim:

1. The chondrogenic inductive agent, comprising a substantially pure polypeptide having the following characteristics:
    (a) extractable from dentin;
    (b) having an apparent relative molecular weight ($M_r$) in non-aggregated form in the range from 6,000 to about 8,500, as determined by gel filtration chromatography;
    (c) an isoelectric pH within the range from 4.5 to 6.5; and
    (d) capable of inducing muscle fibroblast cells in vitro to enhanced production of cartilage-specific proteoglycan and Type II collagen.

2. A substantially pure polypeptide having an apparent relative molecular weight ($M_r$) of approximately 8,000 and an isolation pH of substantially 5.5 to 6.0, and characterized as a chondrogenic inductive agent by being capable of inducing muscle fibroblast cells in vitro to enhanced production of cartilage-specific proteoglycan and Type II collagen, said polypeptide being extractable from dentin.

* * * * *